United States Patent
Abdelgawad et al.

(10) Patent No.: US 9,949,772 B2
(45) Date of Patent: Apr. 24, 2018

(54) INTERNAL BONE LENGTHENER DEVICE AND METHOD OF USE THEREOF

(71) Applicants: TEXAS TECH UNIVERSITY SYSTEM, Lubbock, TX (US); THE BOARD OF REGENTS, THE UNIVERSITY OF TEXAS SYSTEM, Austin, TX (US)

(72) Inventors: Amr Abdelgawad, El Paso, TX (US); Noe Vargas-Hernandez, El Paso, TX (US); Khaled Emara, Cairo (EG); Mario E. Rodriguez, Chihuahua Juarez (MX)

(73) Assignees: Texas Tech University System, Lubbock, TX (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/315,248

(22) PCT Filed: May 29, 2015

(86) PCT No.: PCT/US2015/033393
§ 371 (c)(1),
(2) Date: Nov. 30, 2016

(87) PCT Pub. No.: WO2015/184397
PCT Pub. Date: Dec. 3, 2015

(65) Prior Publication Data
US 2017/0100173 A1  Apr. 13, 2017

Related U.S. Application Data

(60) Provisional application No. 62/005,691, filed on May 30, 2014.

(51) Int. Cl.
*A61B 17/80* (2006.01)
*A61B 17/00* (2006.01)

(52) U.S. Cl.
CPC ...... *A61B 17/8004* (2013.01); *A61B 17/8057* (2013.01); *A61B 2017/00075* (2013.01);
(Continued)

(58) Field of Classification Search
CPC ............ A61B 17/8004; A61B 17/8057; A61B 2017/00075; A61B 2017/00199;
(Continued)

(56) References Cited

U.S. PATENT DOCUMENTS

2005/0234448 A1* 10/2005 McCarthy .......... A61B 17/8004
606/57
2008/0172063 A1*  7/2008 Taylor .................... A61B 17/66
606/105
2012/0245636 A1*  9/2012 Dall ................... A61B 17/7016
606/246

FOREIGN PATENT DOCUMENTS

WO    WO 2009062522 A2 *  5/2009   ......... A61B 17/8004

* cited by examiner

*Primary Examiner* — Pedro Philogene
*Assistant Examiner* — David C Comstock
(74) *Attorney, Agent, or Firm* — Dickinson Wright PLLC; Ross Spencer Garsson

(57) ABSTRACT

An extramedullary bone lengthener and use thereof that is an internal device that does not require nailing. The invention includes a telescoping plate that attaches to the upper and lower portions of the bone via screws; a small motor affixed on or within the plate. This motor, controlled remotely, will controllably lengthen the plate, thus lengthening the bone. The bone will be cut (osteotomy) then the plate will be applied to both ends and fixed to each end with screws. The
(Continued)

motor will be controlled from outside by a remote control which will allow the plate to expand causing lengthening of the attached bone.

30 Claims, 14 Drawing Sheets

(52) U.S. Cl.
CPC ............... *A61B 2017/00199* (2013.01); *A61B 2017/00212* (2013.01); *A61B 2017/00398* (2013.01); *A61B 2017/00734* (2013.01); *A61B 2017/00991* (2013.01)

(58) Field of Classification Search
CPC ........... A61B 2017/00212; A61B 2017/00398; A61B 2017/00734; A61B 2017/00991
USPC ................ 606/60, 62, 63, 68, 281, 282, 105
See application file for complete search history.

INTERNAL BONE LENGTHENER DEVICE AND METHOD OF USE THEREOF

CROSS REFERENCE TO RELATED PATENT APPLICATION

This application claims priority to provisional U.S. patent application Ser. No. 62/005,691, entitled "Internal Bone Lengthener Device And Method Of Use Thereof," filed on May 30, 2014, which is commonly assigned to the Assignee of the present invention and is here hereby incorporated herein by reference in its entirety for all purposes.

FIELD OF INVENTION

The present invention generally relates to medical devices for treating conditions involving the bone growth applications of the skeletal system. More particularly, the present disclosure relates to an implantable and remote controlled medical device designed to help in the process of bone elongation for children with skeletal deformities.

BACKGROUND OF INVENTION

Limb lengthening surgery is an option for individuals who have discrepancies in limb length. Certain health conditions can lead to unequal limb lengths such as birth defects, previous injuries or broken bones, poliomyelitis, cerebral palsy, hip diseases, and muscular defects. See http://www.nlm.nih.gov/medlineplus/ency/article/002965.htm. Common approaches to limb lengthening surgery include external fixation (alone), fully implantable lengthening nails, and a combination of lengthening over nail with external fixation. See http://www.lifebridgehealth.org/RIAO/TheConcept.aspx.

Limb lengthening using external fixation (such as by using the Ilizarov method uniplanar limb reconstruction system) are well-known techniques that has been used for treatment of many complicated conditions as congenital and post traumatic bone deformity, short stature treatment, bone infection and nonunion, after removal of tumors to reconstruct or lengthen the bone and soft tissues. In addition to being used to support a fractured limb, the Ilizarov frame is also commonly used to correct deformity through distraction osteogenesis (also known as distraction callotasis and osteodistraction).

In a general distraction osteogenesis procedure, the bone, if not already fractured, is purposely fractured surgically (corticotomy or osteotomy), and the two segments of bone are gradually distracted apart, which allows new bone to form in the gap therebetween. Generally, the rate of gradually distracting the two segments of bone apart is from half to one millimeter per day till the bone reaches the desired length. If the distraction rate is too quick, there is a risk of non-union. If the distraction rate is too slow, there is a risk that the two segments of bone will completely fuse to each other before the distraction period is complete. When the desired length of the bone is achieved using this process, the bone is allowed to consolidate. Distraction osteogenesis applications are mainly focused on the growth of the femur or tibia, but may also include other bones, like the humerus.

Distraction osteogenesis using external fixators has been done for many years. Such a procedure is done by the use of external fixation, which is bulky and with pins attached to the bone and coming out of the skin. Then the fixation need to stay till full consolidation of the new soft bone that was formed and full calcification which usually take about double the duration of lengthening. By way of example, seven centimeters lengthening by the external fixation would generally need to stay for about 7 months or more. Images of distraction osteogenesis using external fixators is depicted in FIGS. 1A-1B.

The external fixator can be unwieldy for the patient. It can also be painful, and the patient is subject to the risk of pin track infections, joint stiffness, loss of appetite, depression, and other side effects. Having the external fixator in place also delays the beginning of rehabilitation.

In response to the shortcomings of external fixator distraction, intramedullary distraction nails have been surgically implanted which are contained entirely within the bone. These are referred to as intramedullary (inside the bone) lengtheners. An image of distraction osteogenesis using an intramedullary distraction nail is depicted in FIG. 1C. In some embodiments, these devices are automatically lengthened via repeated rotation of the patient's limb. This can sometimes be painful to the patient, and can often proceed in an uncontrolled fashion. This therefore makes it difficult to follow the strict daily lengthening regime that avoids non-union (if too quick) or early consolidation (if too slow).

Other intramedullary nails have been developed that have an implanted motor and are remotely controlled. In some instances, the motorized intramedullary nails have an antenna that needs to be implanted subcutaneously, thus complicating the surgical procedure, and making it more invasive. These devices are therefore designed to be lengthened in a controlled manner, but due to their complexity, may not be manufacturable as an affordable product. Others have utilized intramedullary distracters containing an implanted magnet, which allows the distraction to be driven electromagnetically by an external stator (i.e., a large electromagnet). U.S. Pat. No. 8,449,543, "Bone Growth Device And Method," issued May 28, 2013, to Pool et al. ("Pool '543 Patent"), discloses an intramedullary lengthening device that includes a housing, a distraction shaft, a permanent magnet, and a lead screw. The permanent magnet is configured for rotation relative to the housing with the permanent magnet operatively coupled to a lead screw with a threaded portion that can extend the distraction shaft.

There are a number of criteria that must be present for the use of these nails. This criteria includes: wide bone medulla to put these large nails inside, no bone deformity or curve, and skeletally mature bone as in adults (because the nail will destroy the growth plate in children bone), so these nails cannot be used for bone lengthening in children. Another common problem is the mechanical failure of the nail or nail jamming Also these nails are very expensive.

The concept of extramedullary lengtheners (on the surface of the bone) is also known in the prior art and these can be used for children, as opposed to intramedullary lengtheners. This is because intramedullary lengtheners involve the growth plates in both the femur and the tibia. For example, antegrade cannulization, i.e., inserting a tube into a hollow inside of a bone, of the femur not only disrupts the greater trochanter growth plate, but can also lead to avascular necrosis of the femoral head in children and certainly can disrupt growth quite significantly in the tibia, if the children's growth plates are open. Another issue is that intramedullary channels in children have small diameters that often do not leave sufficient room for intramedullary lengthening devices.

U.S. Patent Appl. Publ. No. 2005/0234448, published Oct. 20, 2005, to McCarthy is a prior art example of an extramedullary lengthener. The McCarthy device features extramedullary elongation devices for lengthening one or more bones, the devices implanted adjacent to the bone and under the skin of a patient using minimally invasive techniques. The device includes a frame having smooth edges and an end with a smooth contour, a first plate attached to the frame and configured to be secured to the bone, the first plate having smooth edges, a second plate configured to be secured to the bone, the second plate having smooth edges, a rod (which may be enclosed by the frame) linked to the first plate, an actuator secured either to the rod or the second plate, and a block secured to the second plate, the block linked to the rod such that actuation of the actuator results in displacement of the second plate relative to the first plate.

The McCarthy device does not require exposed hardware (that can lead to infection) or skin and muscle penetration from the pins (that cause pain), and produce minimal scarring from pin sites because the devices are placed under the skin of a patient using minimally invasive techniques. The McCarthy device can be designed with smooth contours to enable implantation using minimally invasive techniques. The devices can be actuated using an actuator that is externally or internally powered. In the case of external power, the McCarthy device can be powered remotely through high frequency transmission of power through the skin.

Another example of an extramedullary lengthener is disclosed in Pool '543 Patent. The Pool device can alternatively be applied to distractible bone plates that are not located within the intramedullary canal, but are external to the bone.

U.S. Pat. No. 5,902,304, issued May 11, 1999 to Walker et al. is a telescopic bone plate for distracting osteotomically separated bone sections. The telescopic bone plate consists of a top bone plate and a bottom bone plate longitudinally, laterally and vertically adjustable relative to each other and including a device for fastening the telescopic bone plate to bone. The Walker device has a telescopic member that adjusts the relative positions of the top and bottom bone plate to each other. The Walker device telescopic member is actuated internally to the patient and may be actuated intraorally in one variation.

PCT Int'l Pat. Appl. Publ. No. WO2009/062522, "E-Plate (Bone Lengthening Plate), published May 22, 2009, to Emara et al. (the "PCT '522 Application") discloses a fixator distraction device is also put internally and rests on the surface (rather than inside) the bone and is remotely controlled from the outside. This extramedullary lengthener device was directed to a wide variety of patients including children and those patients having small bone size, who are the most common type of patients that would need limb lengthening. While the PCT '522 Application discloses that a special small motor is to be connected to the telescopic power crew to elongate the device, and that this motor is remotely controlled from the outside this application does not reveal the manner in which the elongation is effectuated and the mechanisms that are to be implemented to controllably elongate the device.

SUMMARY OF INVENTION

The present invention relates to a bone lengthener and use thereof that is an internal device that does not require nailing. The invention includes a telescoping plate that attaches to the upper and lower portions of the bone via screws; a small motor affixed on or within the plate. This motor, controlled remotely, will controllably lengthen the plate, thus lengthening the bone. A locking system will be used in this expansion mechanism. The bone will be cut (osteotomy) then the plate will be applied to both ends and fixed to each end with screws. The motor will be controlled from outside by a remote control which will allow the plate to expand causing lengthening of the attached bone.

This internal bone lengthener will represent a leap in viable treatment for leg lengthening in children. Because intramedullary lengtheners are not viable for children (due to their open physis (growth plate), narrow sized medulla and possibility of affection of the blood supply to the femoral head (see before), typically, leg lengthening in children is accomplished by external fixation. Despite effectiveness, external fixators are not ideal for children because pins must run from the fixator, through the skin, into the bone; these pins increase the risk for infection, and are generally hard for children to tolerate. Furthermore, children with external fixators tend to avoid contact with others because of the stigma associated with the device. Internal lengthening nails do solve the problems associated with external fixation, but cannot be used in children with open growth plates and narrow medullas. The disclosed invention solves these prior issues; it is an internal device that lengthens without pins or nails.

In general, in one aspect, the invention features an internal bone lengthener device. The internal bone lengthener device includes a base. The internal bone lengthener device further includes a first plate coupled to the base and having a first axis. The first plate is operable to be fixed to the first bone segment along the first axis using one or more first fastening devices. The internal bone lengthener device further includes a second plate slidably coupled to the first plate. The second plate can move in a linear direction relative to the first plate along the first axis. The second plate is operable to be fixed to the second bone segment along the first axis using one or more second fastening device. The base, first plate, and second plate form a contained enclosure within the internal bone lengthening device such that the internal bone lengthener device is operable for use extramedullary to the first bone segment and second bone segment and under the skin of the patient. The internal bone lengthener device further includes a power source coupled to the base and located within the contained enclosure. The internal bone lengthener device further includes an encoder coupled to the power source and located within the contained enclosure. The internal bone lengthener device further includes a motor and transmission coupled to the power source and located within the contained enclosure. The internal bone lengthener device further includes a leadscrew coupled to the motor and transmission and locating within the contained enclosure. The motor and transmission are operable for rotating the leadscrew in a first rotation direction and a second rotation directed. The leadscrew is operably coupled to the first plate and the second plate such that (A) the rotation of the leadscrew in the first rotation direction moves the second plate relative to the first plate along the first axis to elongate the internal bone lengthening device, and (B) the rotation of the leadscrew in the second rotation direction moves the second plate relative to the first plate along the second axis to shorten the internal bone lengthening device. The internal bone lengthener device further includes a PCT board coupled to the power source. The PCT board is operable to transmit and receive an RF signal, to allow the elongation and the shortening of the internal bone lengthening device, and to protect the system from motor reverse voltages.

Implementations of the invention can include one or more of the following features:

The PCT board can include a microcontroller, a H-bridge unit, and a plurality of diodes.

The microcontroller can include an RF transmitter and receiver.

The H-bridge unit can include a H-bridge SMD device to allow elongation and shortening of the internal bone lengthening device.

The plurality of diodes can be operable to protect the internal bone lengthener device from motor reverse voltages.

The encoder can be operable for indicating position of the motor.

The encoder can be operable to count the number of turns of the motor and provide this counted number to the microprocessor. The microprocessor can be operable to determine the length of the internal bone lengthener device based upon the counted number received from the encoder.

The microprocessor can be operable for transmitting the determined length of the internal bone lengthener device to a device remote from the internal bone lengthener device.

The microprocessor can be operable for receiving a signal from a remote control device. The signal can provide instructions to the microprocessor for elongating or shortening the length of the internal bone lengthener device.

The instructions comprise transferring of power from the battery to the H-bridge device. The H-bridge device can be operable for sending signals to the motor and the encoder.

The motor can be operable for activating and moving the transmission.

The transmission can be operable for amplifying torque of the motor such that the torque is above the locking force limit of the leadscrew to produce rotation of the leadscrew in the first rotation direction or the second rotation direction.

The internal bone lengthener device has a first length when the internal bone lengthener device is fully undistracted. The internal bone lengthener device has a second length when the internal bone lengthener device is fully distracted. The ratio of the first length to the second length can be between 1:2 and 4:5.

The maximum height of the internal bone lengthener device can be at most 2 cm. The maximum width of the internal bone lengthener device can be at most 3 cm.

The one or more first fastening devices can be one or more first screws. The one or more second fastening devices can be one or more second screws. The first plate can have one or more first holes through which the one or more first screws can be attached to the first plate and the first bone segment. The second plate has one or more second holes through which the one or more second screws can be attached to the second plate and the second bone segment.

Each of the one or more first screws can be a polyaxial locked screw or a monoaxial locked screw. Each of the one or more second screws can be a polyaxial locked screw or a monoaxial locked screw.

The internal bone lengthener device can further include a locking mechanism to lock the first plate and second plate to prevent slidable movement along the first axis.

Each of the base, first plate, and second plate can include a material that is a titanium alloy material.

The internal bone lengthener device can further include a sealing material layer between the first plate and the second plate. The sealing material can be operable to prevent migration of body fluids of the patient or other contamination into the contained enclosure.

The first plate and the second plate can be slidably connected in a telescopic structure.

In general, in another aspect, the invention features a method that includes the step of selecting an internal bone lengthening device as set forth above. The method further includes the step of fixing the internal bone lengthening device under the skin of the patient. A first plate of the internal bone lengthening device is fixed to a first bone segment of a patient. A second plate of the internal bone lengthening device is fixed to a second bone segment of the patient. The method further includes the step of controlling length of the internal bone lengthening device wirelessly using a remote device. The method further includes the step of obtaining feedback from the internal bone lengthening device wirelessly to monitor the length of the internal bone lengthening device.

Implementations of the invention can include one or more of the following features:

The internal bone lengthening device can be controlled to elongate the length of the internal bone lengthening device during a bone growth process to grow bone between the first bone segment and second bone segment.

The internal bone lengthening device can be controlled to shorten the length of the internal bone lengthening device to compress soft callus during the bone growth process.

The patient can be a child.

The feedback can be displayed on a computer display.

The feedback can be analyzed to monitor patient status.

The monitoring of patient status can be performed in real time.

The method can further include the step of uploading the feedback to a database accessible over the internet that provides a physician or other caretaker an ability to check status of the patient remotely and in real time.

Distraction rate of the internal bone lengthening device can be programmable.

The distraction rate can be controlled on a basis selected from the group consisting of daily, weekly, and monthly.

BRIEF DESCRIPTION OF THE DRAWINGS

For better understanding of the present invention, and the advantages thereof, reference is now made to the following descriptions taken in conjunction with the accompanying drawings.

DETAILED DESCRIPTION

The present invention relates to an implantable and remote controlled medical device designed to help in the process of bone elongation for children with skeletal deformities. The medical device is an implantable, miniaturized, and remote controlled distraction osteogenesis device.

Figure 1A:
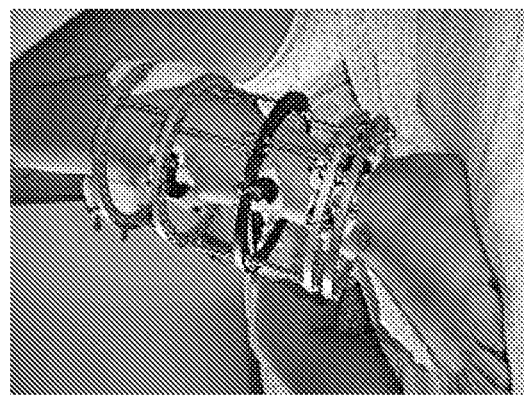
FIGS. 1A-1B illustrates prior art external bone lengthener devices. Such devices are bulky, obstacles when walking, and nuisances while sleeping. They also provide a high risk of infection.
Figure 1B:
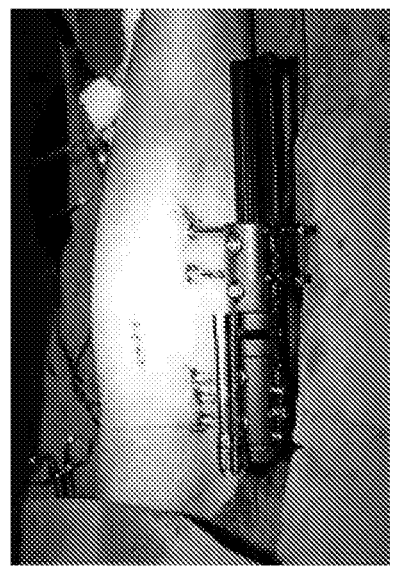
Figure 1C:
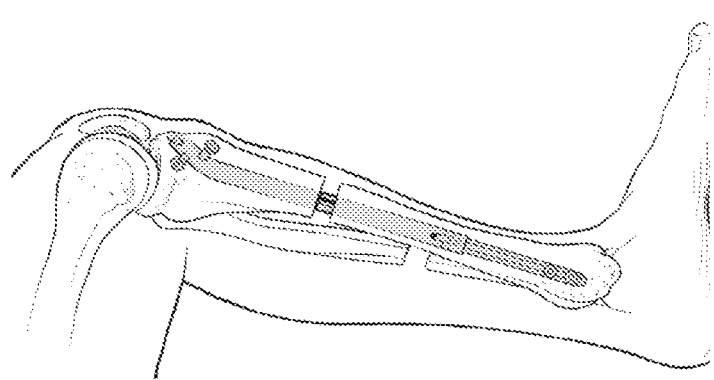
FIG. 1C illustrates a prior art internal bone lengthener device. Such device can destroy the bone growth plate of children and may be too large for use in children or small adults.
Figure 2:
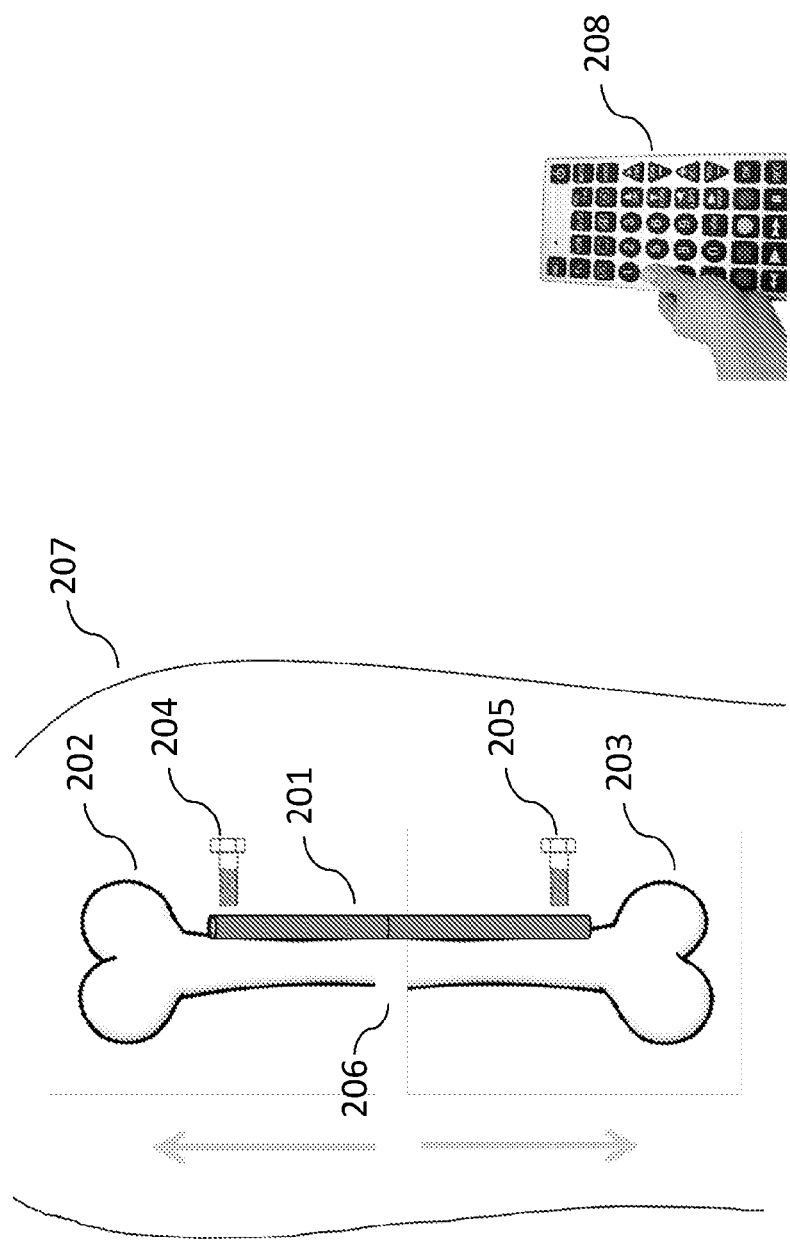
FIG. 2 illustrates an embodiment of the present invention, which includes the internal bone lengthener device and a remote control device.

Referring to the Figures, FIG. 2 illustrates an embodiment of the present invention, which includes the internal bone lengthener device 201 attached to bone segments 202 and 203 of a leg 207 bone screws 204 and 205 and a remote control device 208 that can be used to control the internal bone lengthener device 201. Bone segments 202 and 203 are separated by gap 206. The new bone is to be formed in this gap 206. While the bone growth is occurring, the distance between the bone segments 202 and 203 is increased using the internal bone lengthener device 201 through the remote control device 208.

Figure 3:
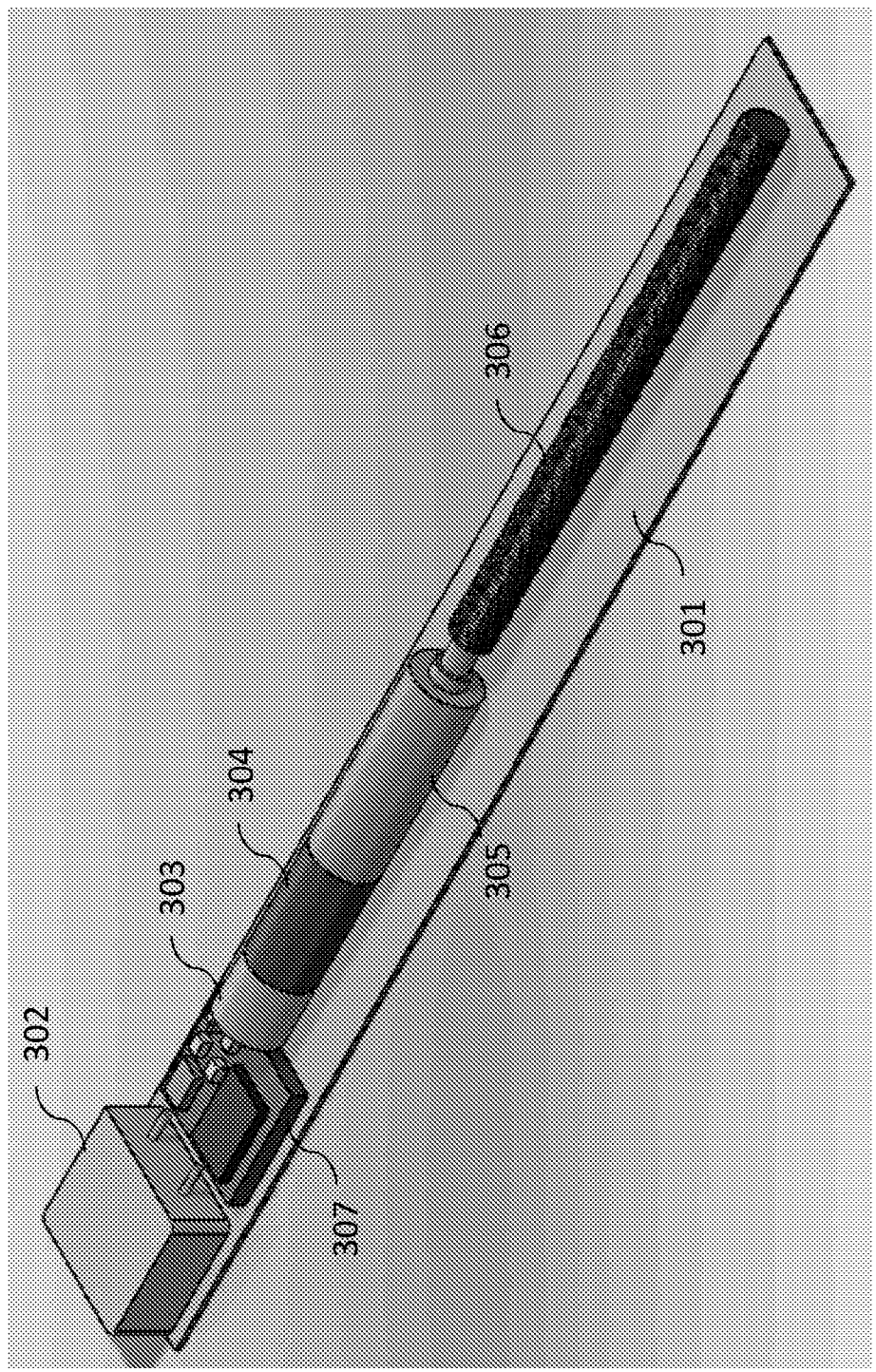
FIG. 3 illustrates a base of the internal bone lengthener device of an embodiment of the present invention.

FIG. 3 illustrates a base 301 of the internal bone lengthener device 401 (shown in FIGS. 4A-4D). In this embodiment, the internal bone lengthener device includes a battery 302, encoder 303, motor 304, transmission 305, leadscrew 306, PCB board 307 (which PCB board 307 includes at least a microcontroller with RF capacity, H-bridge unit, and diodes).

The motor 304 with an encoder (feedback unit) 303 connected to a transmission 305 amplifies torque which then powers the leadscrew 306. The leadscrew 306 is connected to a nut attached to the other side of the structure. Relative movement of the leadscrew 306 with respect to the threaded section produces the elongation.

Electronic control is provided using the PCB board 307 having soldered components: a microcontroller (with RF transmitter and receiver), an H-bridge SMD device (to allow bidirectional movement) and a number of diodes (i.e., four diodes), which protect the system from motor reverse voltages. The PCB board 307 is connected to battery 302, to the encoder 303, and to the motor 304. Encoder 303 indicates the position of the motor 304 at any time counting fractions of turns; this information is analyzed by the microcontroller and sent to the remote control device 208.

The locking mechanism is due to the nature of the thread features in the leadscrew 306. The thread type locks the mechanism for push or pulling external forces and only reacts/moves when at least a predetermined torque is applied.

These parts can interact as follows: Battery 302 provides power to the PCB board 307 circuitry, the remote control device 208 sends signal to microcontroller's RF receiver to transfer power from the battery 302 to the H-bridge device, which then sends signal to motor 304 and encoder 303. The motor 304 is activated and moves the transmission 305, which amplifies torque to reach the locking force limit of the leadscrew 306 to produce rotation. The leadscrew 306 is connected to a threaded nut in the other side of the structure to produce the relative movement between the leadscrew 306 and the threaded nut or one segment of the structure versus the other segment of the structure. The rotation of the motor 304 is measured and controlled by the encoder 303, which provides information to the microcontroller if more turns are required or to stop (if turns are completed). The transmitter in the microcontroller sends information to the remote control device 208 about how many turns are completed and distraction distance of the leadscrew 306. Diodes in the PCB board 307 protect the circuitry from reverse voltages produces by motor 304 when turned off due to the nature of the inductive load or coil winding motors.

In embodiments of the present invention, sensors can also be included to monitor patient behavior, such as temperature and stresses produced in the affected area.

Figure 4A:
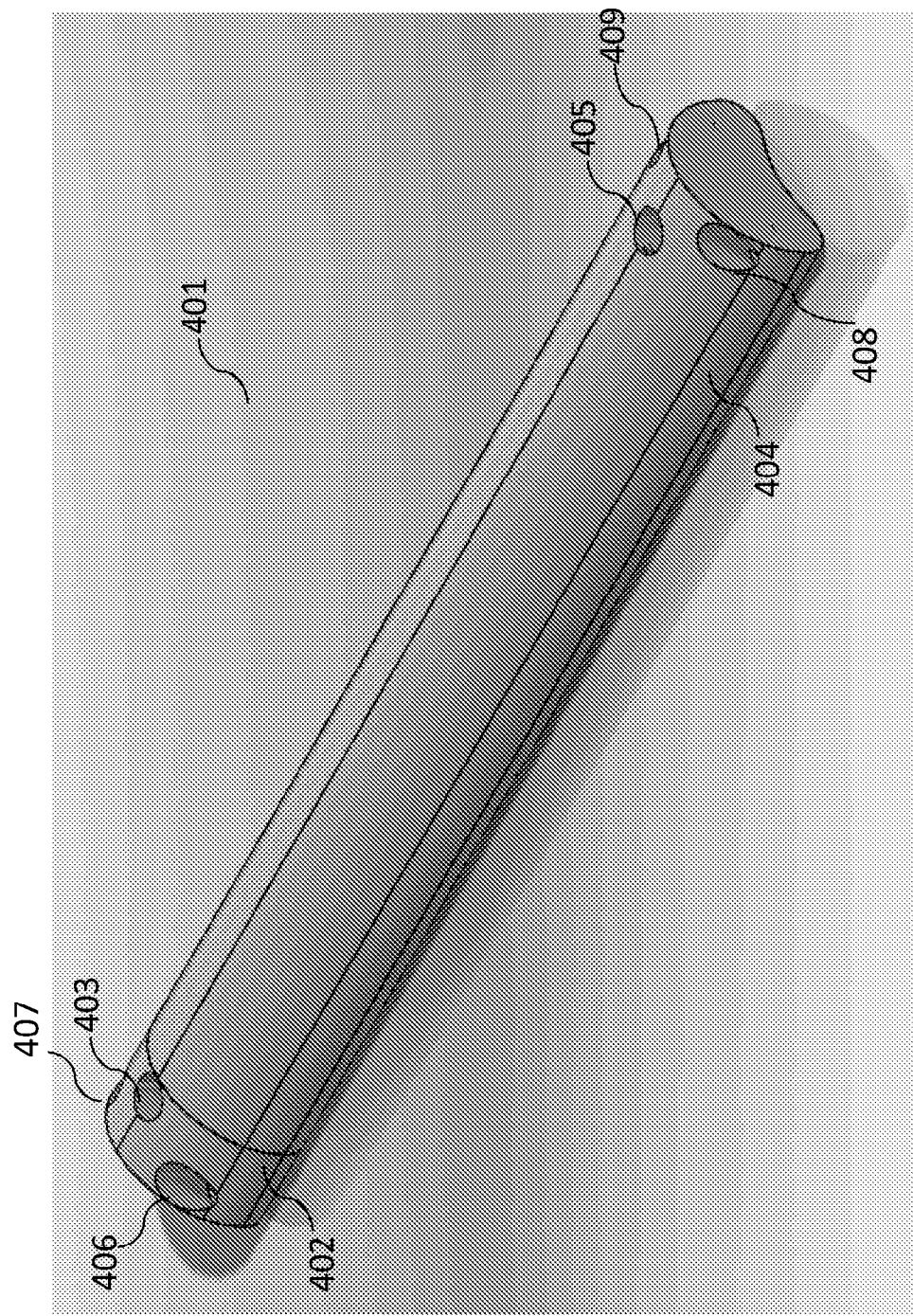
FIGS. 4A-4D are different perspective views of an internal bone lengthener device of an embodiment of the present invention.
Figure 4B:
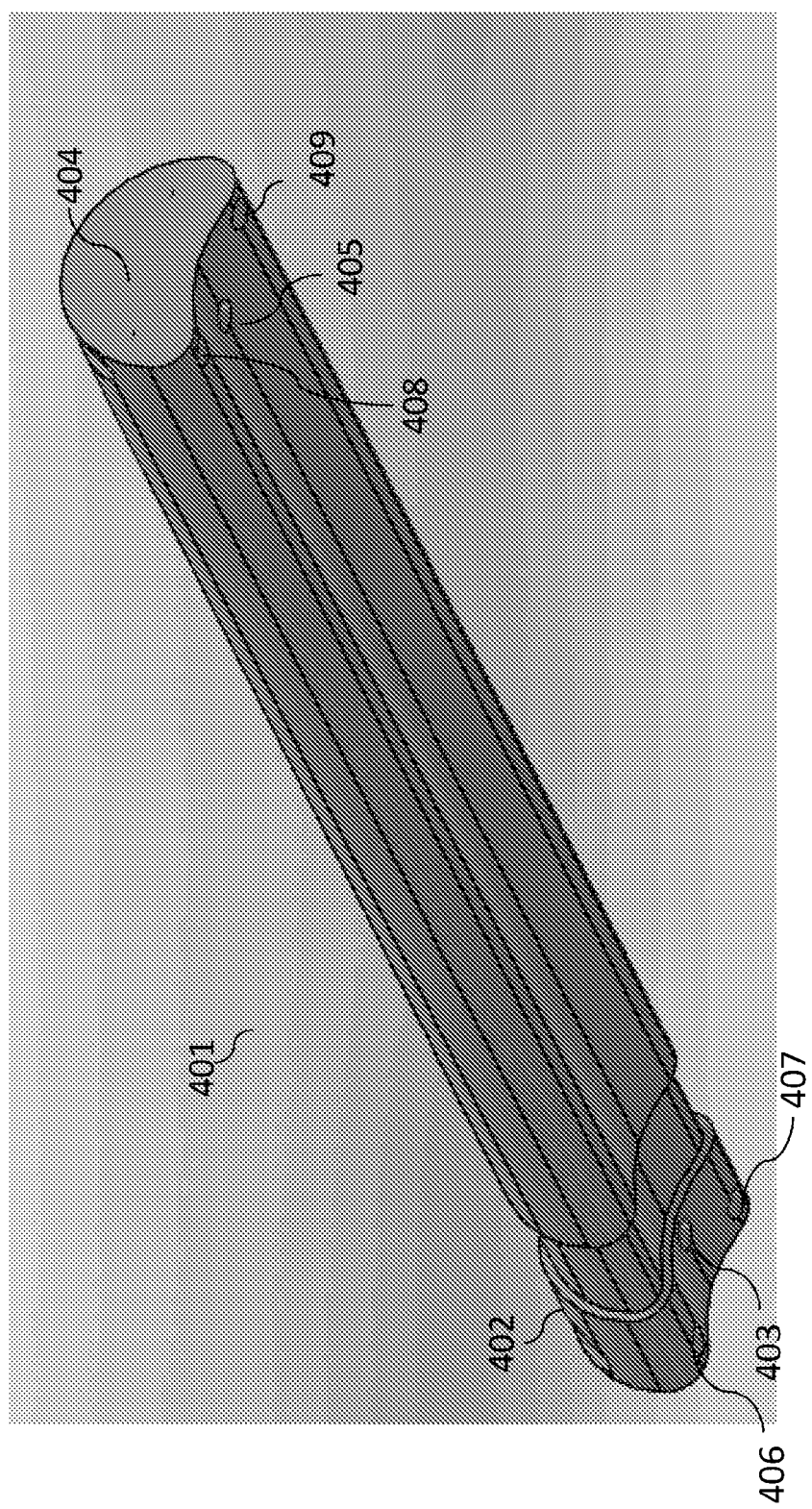
Figure 4C:
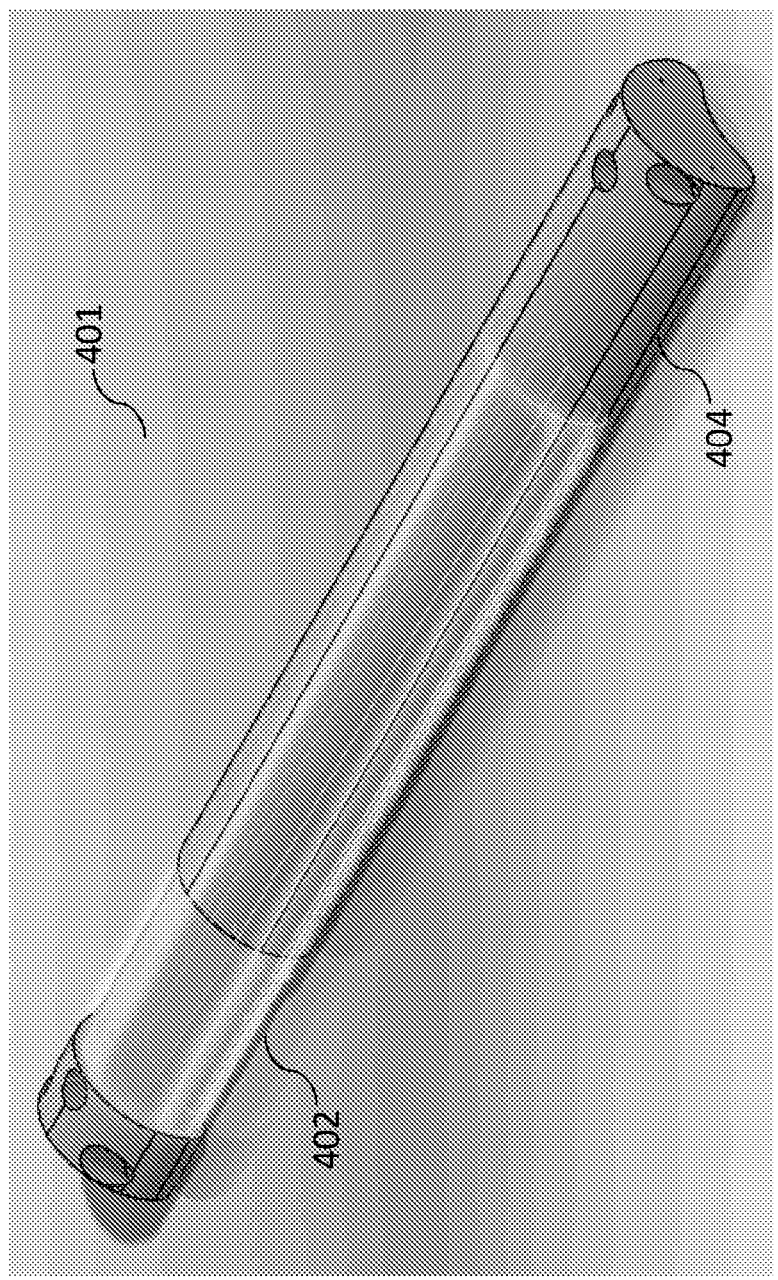
Figure 4D:
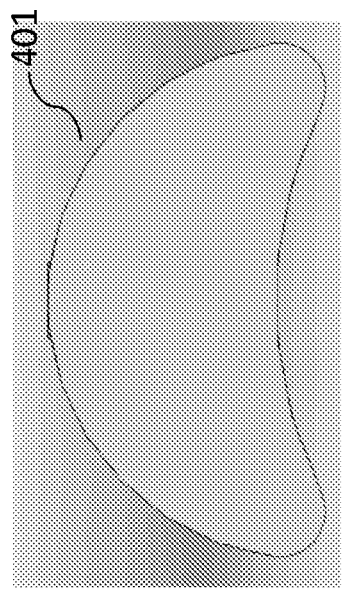

FIGS. 4A-4D are different perspective views of an internal bone lengthener device 401. In this instance, there is a pair of plates 402 and 404. These plates are slidably connected in that the plates 402 and 404 can move in a linear direction relative to each other. FIGS. 4B-4C further illustrate plates 402 and 404 and their slidable connection. FIG. 4D is an end view perspective internal bone lengthener device 401, which shows the shape of the plates 402 and 404. The shapes of plates 402 and 404 are designed to better adapt to the bone geometry with the bone segments to which the internal bone lengthener device 401 is to be attached so as to enhance fixation.

In embodiments of the present invention, the ratio of the length of the undistracted device to the length of the completely distracted device is generally in the range between 1:2 to 4:5, and more generally around 3:4. In one embodiment of the present invention, the length of the undistracted device was 176.4 mm and the length of the completely distracted device was 236.4 mm.

Furthermore the height of the device was less than 2 cm and the maximum width was less than 3 cm. In one embodiment of the present invention, the maximum height was 17.25 mm and the maximum width was 27.41 mm. For such embodiment, the screws used to secure plates 402 and 404 through holes The present invention can be fixed directly to the bone without the need of an intermediate plate. I.e., no intermediate plate is needed or required (as compared to the PCT '522 Application devices in which an intermediate plate was fixed to the bone and the plate of that device was then fixed to the intermediate plate).

Plate 402 has holes 403, 406, and 407, and plate 404 has holes 405, 408, and 409, through which the fastening devices (screws) can be used to attach each of plates 402 and 404 to the two bone segments independently.

In the embodiment having: the length of the undistracted device of 176.4 mm, the length of the completely distracted device of 236.4 mm, the maximum height of 17.25 mm, and the maximum width of 27.41 mm, the screws used to secure plates 402 and 404 (through holes 403, 405, 406, 407, 408, and 409) had a body diameter of 3.5 mm and a head diameter of 6 mm.

Structure size can be modified depending on patient needs. If more than 6 cm of distraction distance is required, the total length of the structure can increase the same distance. The opposite is also possible to make the structure shorter and address less than 6 cm distraction distance if required.

The fastening devices (screws) shown in FIG. 2 lock the plates 402 and 404 of the internal bone lengthener device 401 to secure stability and there is no need for friction force to stabilize the plates 402 and 404 to the surface of the bone segments. The screws can be polyaxial locked screws or monoaxial locked screws.

Figure 5:
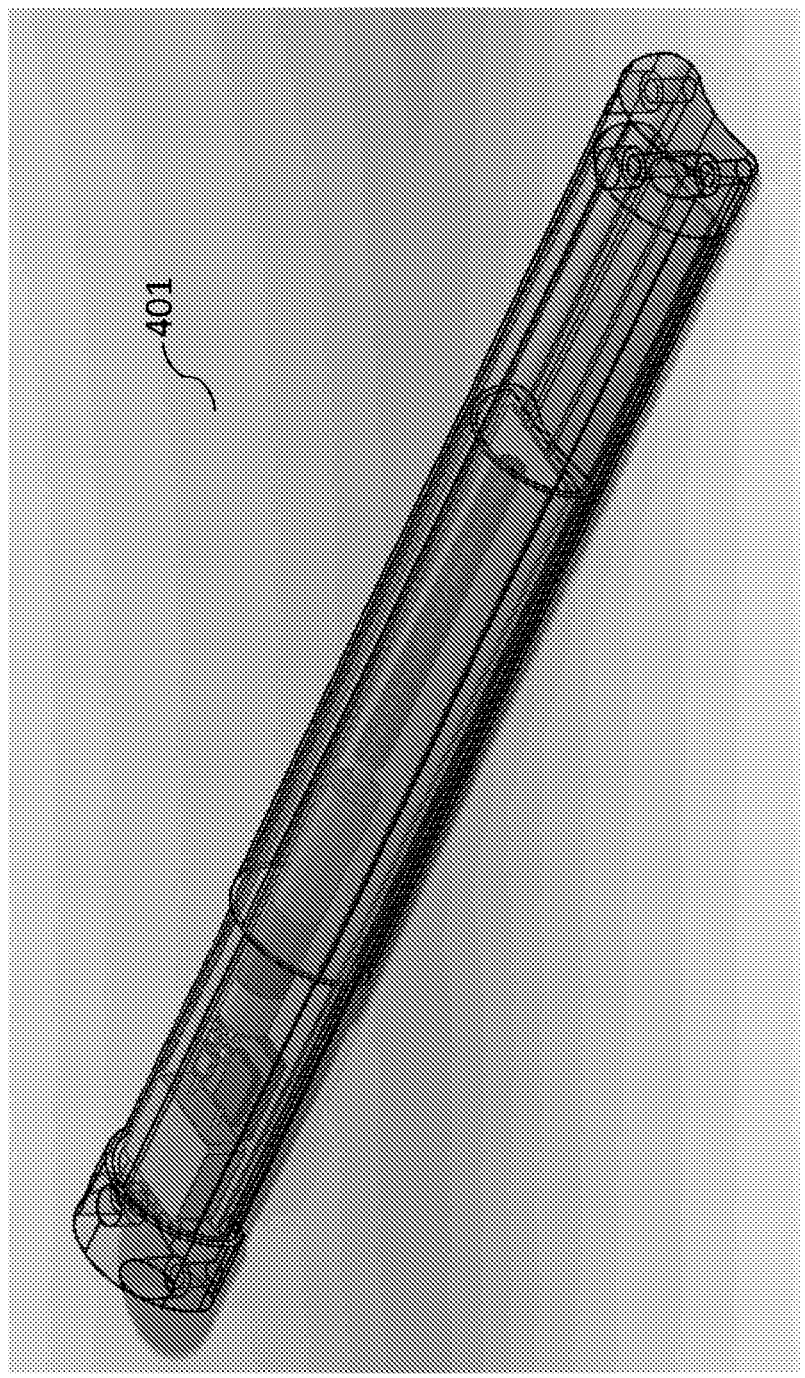
FIGS. 5 and 6 are illustrations of transparent views of the internal bone lengthener device of FIGS. 4A-4D.
Figure 6:
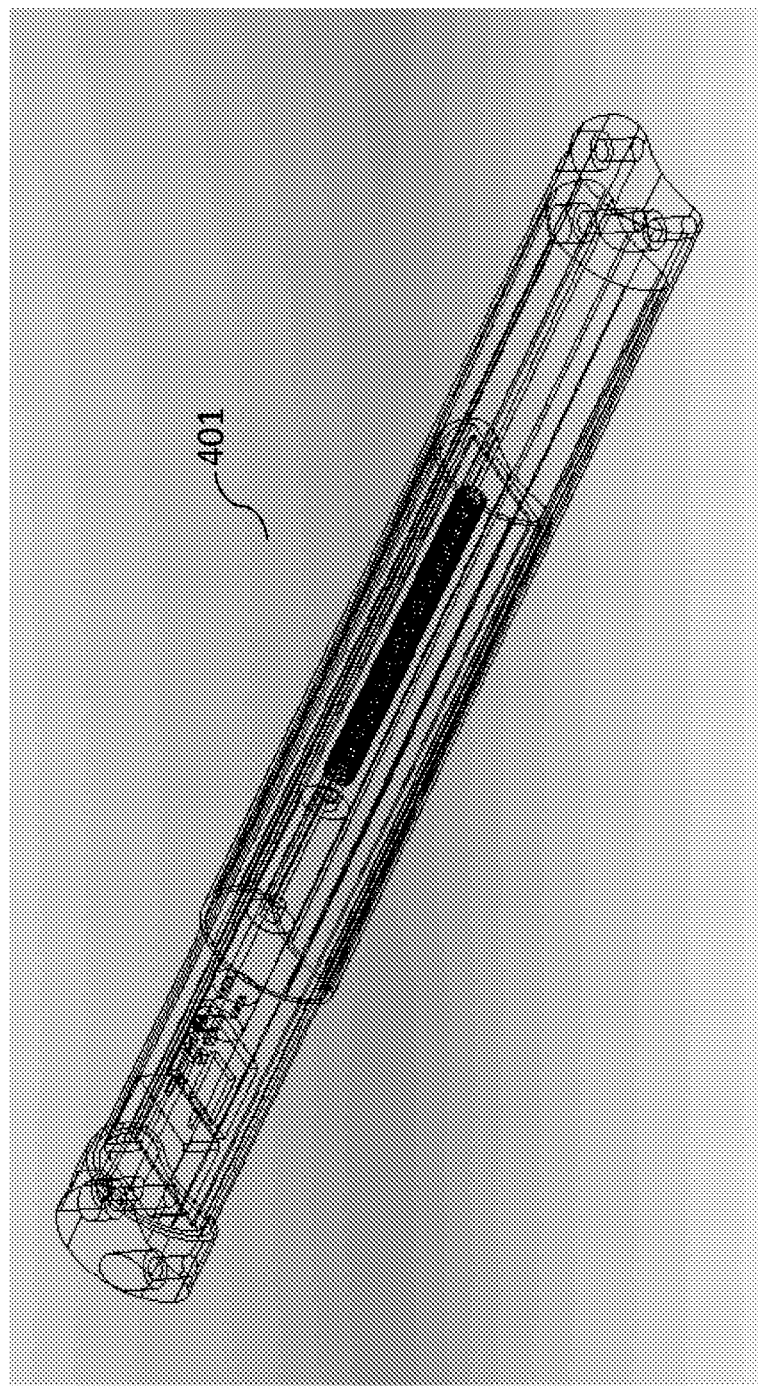

FIGS. 5 and 6 are illustrations of transparent views of the internal bone lengthener device 401 of FIGS. 4A-4D. The transparent views of the plates 402 and 404 provide a view of the base 301 and the internal parts shown in FIG. 3 as they are positioned within the internal bone lengthener device

401. The base 301 internal parts shown in FIG. 3 are mounted inside plates 402 and 404, which will be fixed to the bone segments using screws at the ends (in holes 403 and 405, respectively).

Figure 7A:
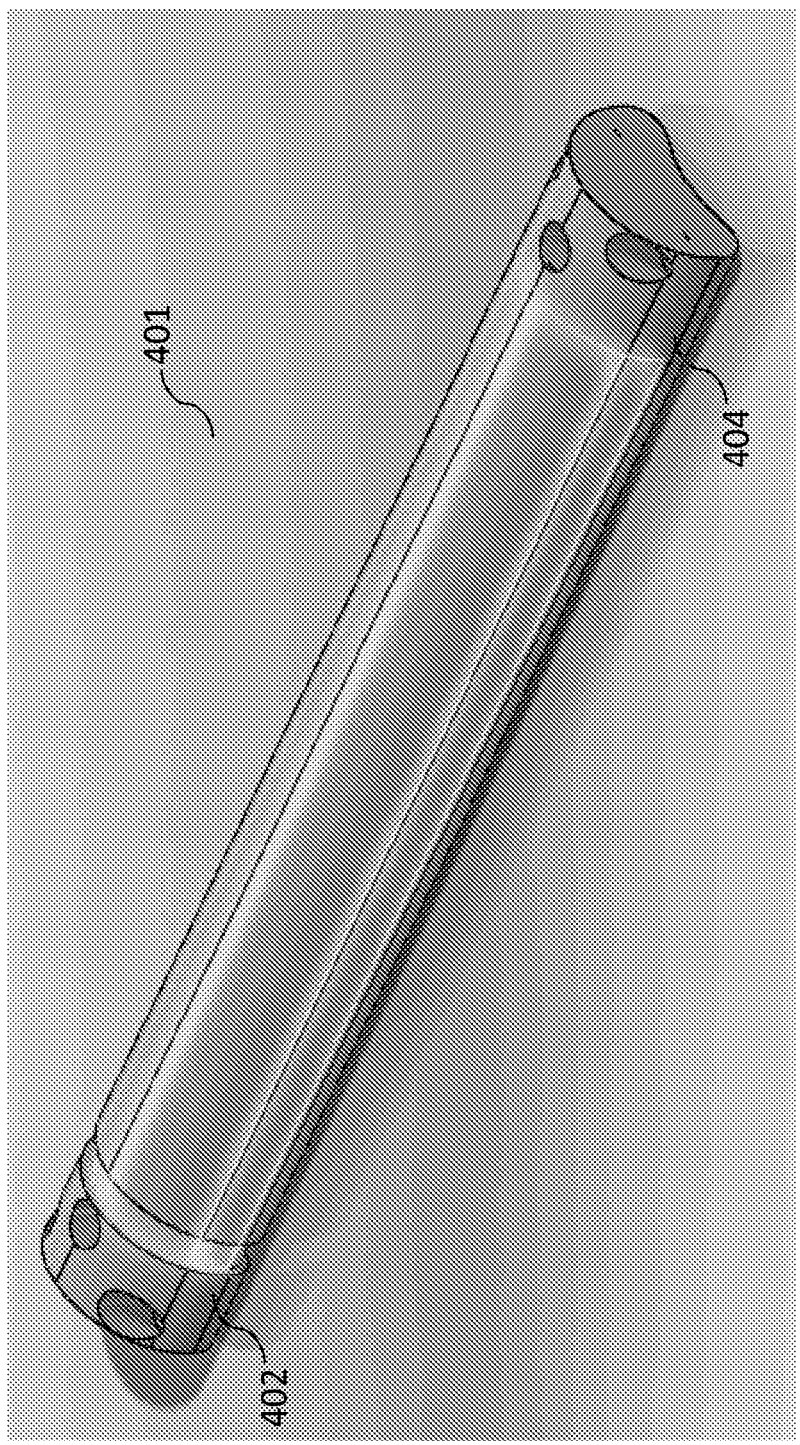
FIGS. 7A-7C are illustrations of the internal bone lengthener device of FIGS. 4A-4D as the telescoping mechanism extends the internal bone lengthener device.
Figure 7B:
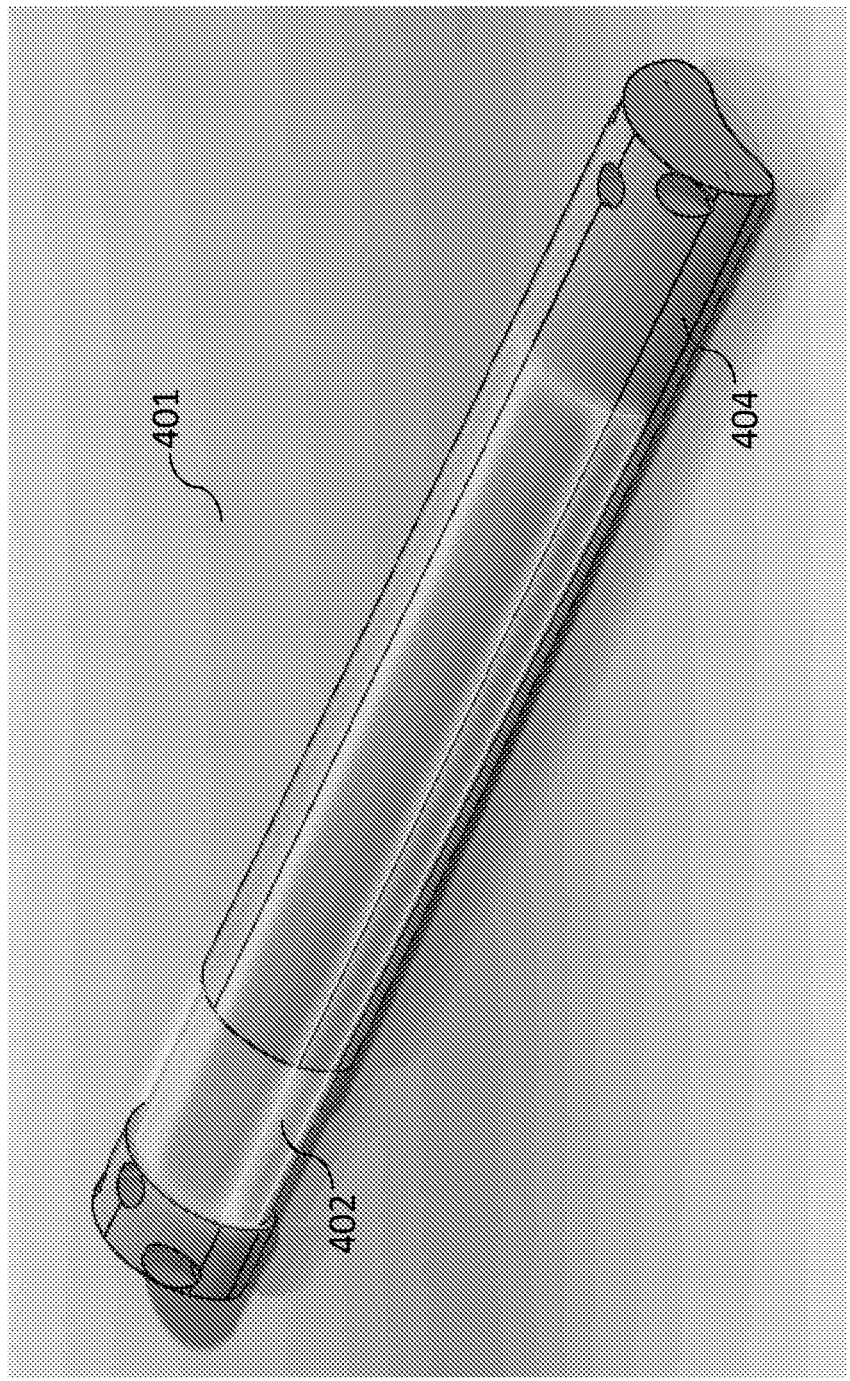
Figure 7C:
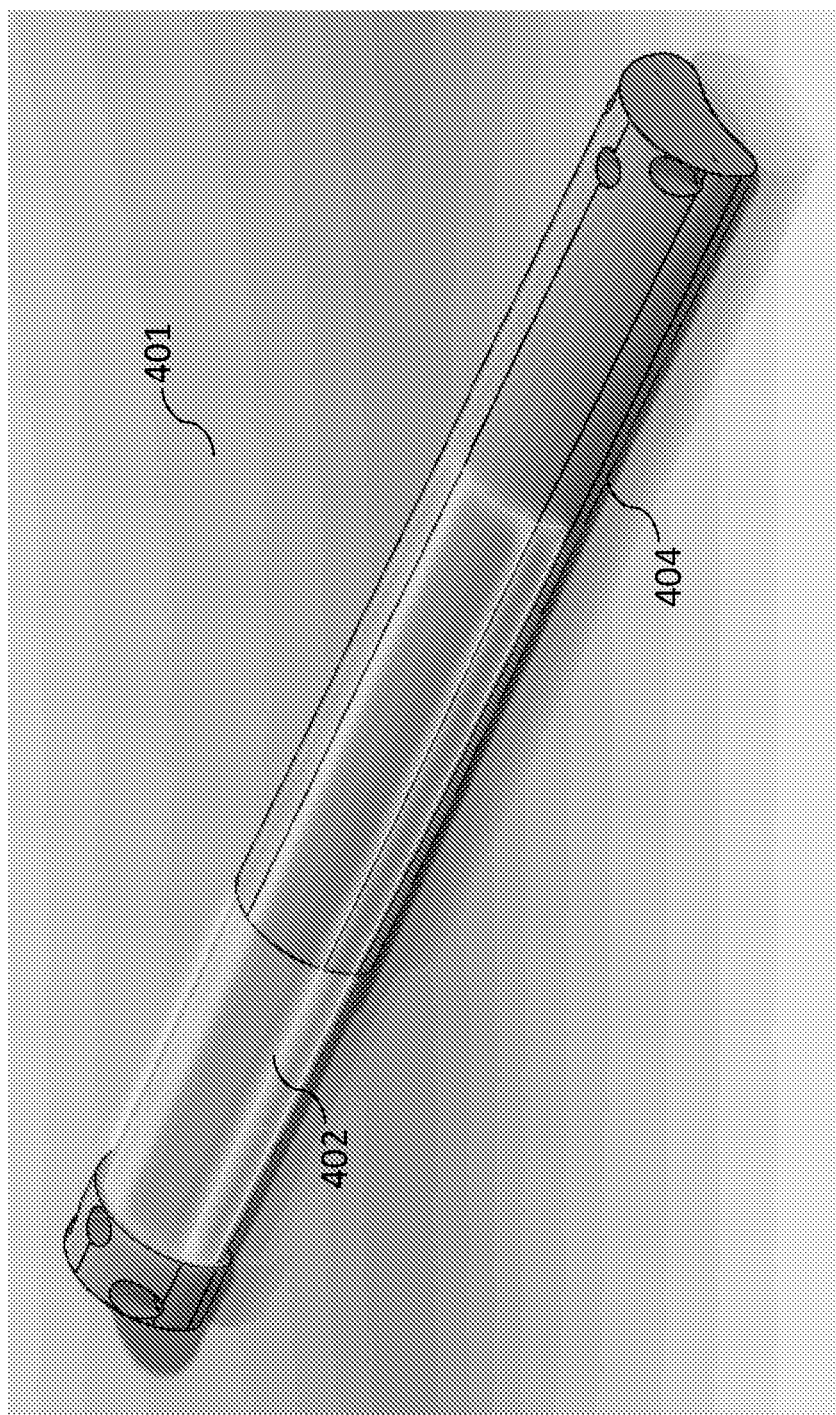

FIGS. 7A-7C are illustrations of the internal bone lengthener device 401 as the telescoping mechanism slidably moves plates 402 and 404 relative to each other, thus extending the internal bone lengthener device 401.

Figure 8:
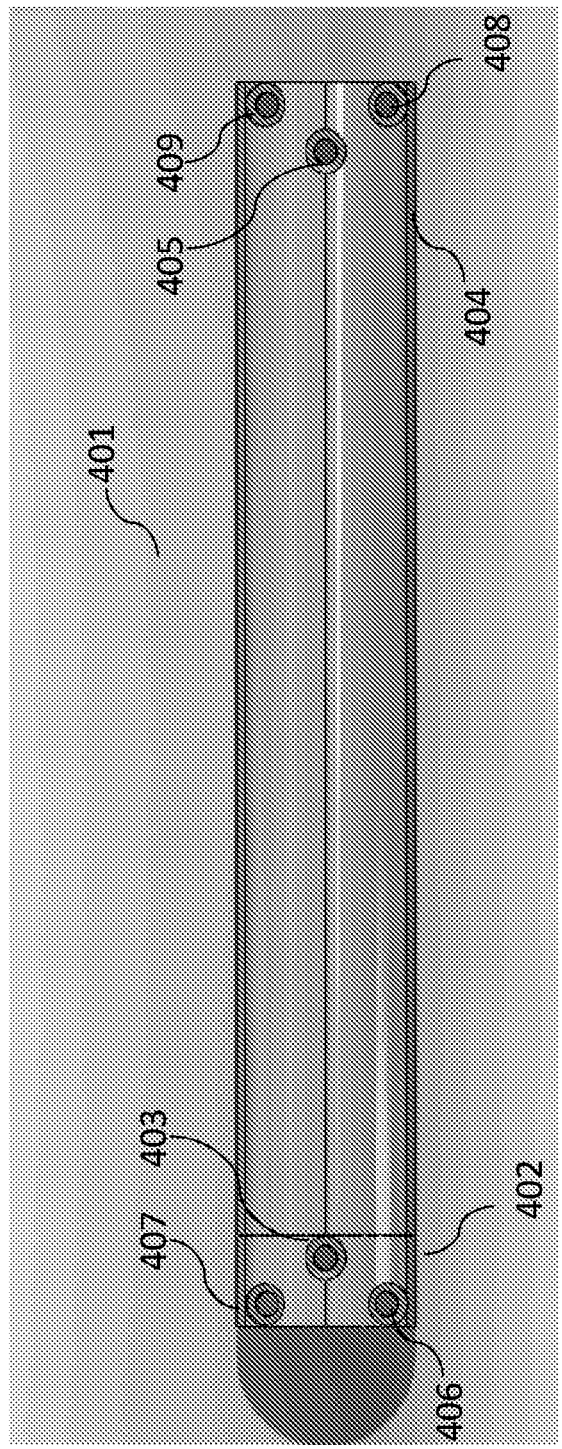
FIG. 8 is an illustration of a top view of the internal bone lengthener device of FIGS. 4A-4D.
Figure 9:
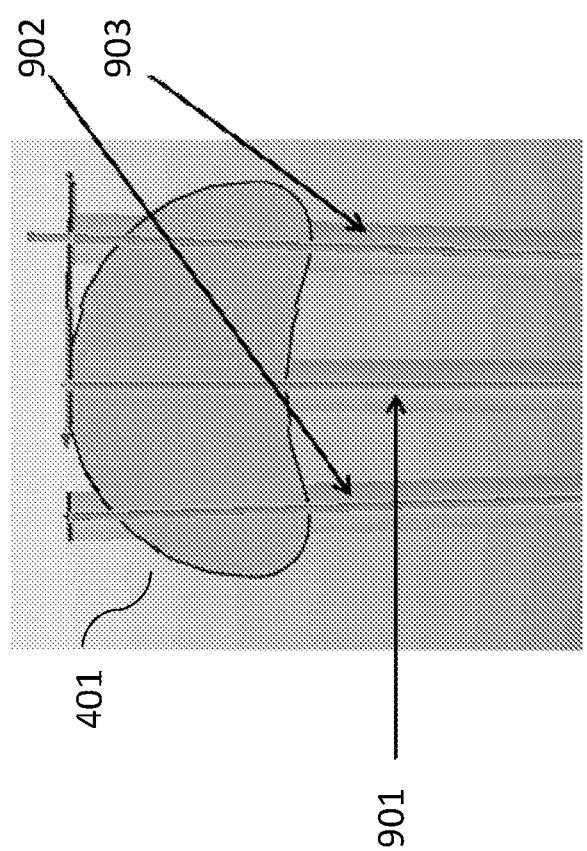
FIG. 9 is an illustration of the screws positioned in the internal bone lengthener device of FIGS. 4A-4D (side view)

FIG. 8 is an illustration of internal bone lengthener device 401 that shows the distribution of holes 403, 405, 406, 407, 408, and 409. Hole 403 and 405 are relatively vertical (i.e., parallel to the height of the internal bone lengthener device 401 such that these will be perpendicular to the surface of the leg bone to which device 401 is to be attached). The remaining holes are inclined at an angle between 1° and 5° (generally around 2°) for improved stress shielding. FIG. 9 illustrates this angle of inclination of the screws 901-903 when inserted through the holes of the device 401. For instance, screw 901 is a vertical screw as it would be positioned though hole 403. Screws 902 and 903 are shown with an angle of inclination, as they would be positioned through holes 406 and 407, respectively.

The osteodistraction system will have the capability to be controlled by wirelessly, such as by radio frequency signals, using a remote control device located outside the body and manipulated by doctor or other caretaker. Information (such as feedback) from the internal bone lengthener device can be transmitted out and received by the remote control device (or other device), which transmitted information can be displayed into screen. Moreover, the control device can include a reverse rotation in case the doctor or other caregiver needs to compress (rather than elongate) the soft callus during the bone growth process.

Features of the present invention and its use can include:
Providing treatment for children in a manner not previously allowed since this could affect their growth plates.
No external physical connections.
No external fixators.
Telescopic structure. (The telescopic structure can include a sealing material layer between the two structure segments to prevent migration of body fluids or contamination inside the osteodistractor).
Bone shape adapted structure profile.
Use screws to get fixed to bone side wall.
Bi-directional rotation movement capacity.
Variable distraction rate capability.
Preset maximum distraction distance (such as between 5 cm to 7 cm, and typically around 6 cm).
Implanted battery included to energize the system.
Miniature electric motor produces torque and mechanical transmission that amplifies torque.
Leadscrew used to produce linear displacement and secure system from involuntary backwards movement.
Microcontroller unit and H-bridge circuitry for intelligence of the system.
Remote controlled (such as by radio frequency (RF) signals approved by FCC for usage in medical implanted devices).
External remote control device that activates implanted device and it is completely controlled by doctor/caregiver (also program can be configured to prevent other users' access).
Movement and position feedback information sent from implanted device to external control or other receiver (which can also include a unit for displaying the information).
Bidirectional rotation movement for elongation or compression (shorten bone) if required.
Titanium alloy material can be utilized in the device to avoid bone atrophy (per Wolff's Law), to enhance bio-compatibility, and to prevent corrosion.

Features of the remote control used in the present invention and its use can include:
Bidirectional communication—signal sent from remote control device to implanted internal bone lengthener device for activation and signal sent from implanted internal bone lengthener device to remote control device to keep track of distance gaining.
Communication frequency range is from 401 to 457 MHz per Federal Communications Commission (FCC) regulations for implantable devices.
Lengthening information recorded in a local database (history of total gaining).
Distraction rate programmable (daily, weekly, monthly) depending on physician's or other caretaker's evaluation.
Information is uploaded to internet to allow physician or other caretaker to check patient status online in real time
Display (such as a 7 inch color display).
Rechargeable with long lasting battery.
For security purposes, physician or other caregiver is the only one authorized to control the unit (such as by password protection, biometric device, etc.).

Additional information of the present invention is included in the thesis "Design And Development Of Implantable And Remote Controlled Distraction Osteogenesis Device For Limb Lengthening Practice In Children," Mario E. Rodriguez, Department of Mechanical Engineering, UTEP (2014). This thesis is incorporated herein in its entirety.

The examples provided herein are to more fully illustrate some of the embodiments of the present invention. It should be appreciated by those of skill in the art that the techniques disclosed in the examples which follow represent techniques discovered by the Applicant to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above.

RELATED PATENTS AND PUBLICATIONS

The following patents and publications relate to the present invention:
U.S. Pat. No. 5,672,177, "Implantable Bone Distraction Device," issued Sep. 30, 1997, to Seldin.
U.S. Pat. No. 5,827,286, "Incrementally Adjustable Tibial Osteotomy Fixation Device And Method," issued Oct. 27, 1998, to Incavo et al.

U.S. Pat. No. 5,902,304, "Telescopic Bone Plate For Use In Bone Lengthening By Distraction Osteogenesis," issued May 11, 1999, to Walker et al U.S. Pat. No. 8,449,543, "Bone Growth Device And Method," issued May 28, 2013, to Pool et al.

U.S. Patent Publication No. 2005/0234448, "Implantable Bone-Lengthening Device," published Oct. 20, 2011, to McCarthy.

PCT Int'l Pat. Appl. Publ. No. WO2009/062522, "E-Plate (Bone Lengthening Plate), published May 22, 2009, to Emara et al.

*Limb Lengthening and Reconstruction Surgery,* 2007, ed. Rozbrunch, S.R., et al., Informa Healthcase ISA, Inc.

Shigley, J. E., et al., 2003, *Mechanical Engineering Design* (7th ed.), McGraw Hill.

Bhandari, V. B., 2007, *Design of Machine Elements*, Tata McGraw-Hill.

The disclosures of all patents, patent applications, and publications cited herein are hereby incorporated herein by reference in their entirety, to the extent that they provide exemplary, procedural, or other details supplementary to those set forth herein.

What is claimed is:

1. An internal bone lengthener device comprising:
   (a) a base;
   (b) a first plate coupled to the base and having a first axis, wherein the first plate is operable to be fixed to the first bone segment along the first axis using one or more first fastening devices;
   (c) a second plate slidably coupled to the first plate, wherein
      (i) the second plate can move in a linear direction relative to the first plate along the first axis,
      (ii) the second plate is operable to be fixed to the second bone segment along the first axis using one or more second fastening device, and
      (iv) the base, first plate, and second plate form a contained enclosure within the internal bone lengthening device such that the internal bone lengthener device is operable for use extramedullary to the first bone segment and second bone segment and under the skin of the patient;
   (b) a power source coupled to the base and located within the contained enclosure;
   (c) an encoder coupled to the power source and located within the contained enclosure;
   (d) a motor and transmission coupled to the power source and located within the contained enclosure;
   (e) a leadscrew coupled to the motor and transmission and locating within the contained enclosure, wherein
      (i) the motor and transmission are operable for rotating the leadscrew in a first rotation direction and a second rotation directed, and
      (ii) the leadscrew is operably coupled to the first plate and the second plate such that (A) the rotation of the leadscrew in the first rotation direction moves the second plate relative to the first plate along the first axis to elongate the internal bone lengthening device, and (B) the rotation of the leadscrew in the second rotation direction moves the second plate relative to the first plate along the second axis to shorten the internal bone lengthening device; and
   (f) a PCB board coupled to the power source, wherein the PCB board is operable to transmit and receive an RF signal, to allow the elongation and the shortening of the internal bone lengthening device, and to protect the system from motor reverse voltages.

2. The internal bone lengthener device of claim 1, wherein the PCB board comprises a microcontroller, a H-bridge unit, and a plurality of diodes.

3. The internal bone lengthener device of claim 2, wherein the microcontroller comprises an RF transmitter and receiver.

4. The internal bone lengthener device of claim 2, wherein the H-bridge unit comprises a H-bridge SMD device to allow elongation and shortening of the internal bone lengthening device.

5. The internal bone lengthener device of claim 2, wherein the plurality of diodes that are operable to protect the internal bone lengthener device from motor reverse voltages.

6. The internal bone lengthener device of claim 1, wherein the encoder is operable for indicating position of the motor.

7. The internal bone lengthener device of claim 6, wherein
   (a) the encoder is operable to count the number of turns of the motor and provide this counted number to the microprocessor;
   (b) the microprocessor is operable to determine the length of the internal bone lengthener device based upon the counted number received from the encoder.

8. The internal bone lengthener device of claim 7, wherein the microprocessor is operable for transmitting the determined length of the internal bone lengthener device to a device remote from the internal bone lengthener device.

9. The internal bone lengthener device of claim 1, wherein the microprocessor is operable for receiving a signal from a remote control device, which signal provides instructions to the microprocessor for elongating or shortening the length of the internal bone lengthener device.

10. The internal bone lengthener device of claim 9, wherein
    (a) the instructions comprise transferring of power from the battery to the H-bridge device; and
    (b) the H-bridge device is operable for sending signals to the motor and the encoder.

11. The internal bone lengthener device of claim 1, wherein the motor is operable for activating and moving the transmission.

12. The internal bone lengthener device of claim 11, wherein the transmission is operable for amplifying torque of the motor such that the torque is above the locking force limit of the leadscrew to produce rotation of the leadscrew in the first rotation direction or the second rotation direction.

13. The internal bone lengthener device of claim 1, wherein
    (a) the internal bone lengthener device has a first length when the internal bone lengthener device is fully undistracted;
    (b) the internal bone lengthener device has a second length when the internal bone lengthener device is fully distracted; and
    (c) the ratio of the first length to the second length is between 1:2 and 4:5.

14. The internal bone lengthener device of claim 1, wherein
    (a) the maximum height of the internal bone lengthener device is at most 2 cm; and
    (b) the maximum width of the internal bone lengthener device is at most 3 cm.

15. The internal bone lengthener device of claim 1, wherein
    (a) the one or more first fastening devices are one or more first screws;

(b) the one or more second fastening devices are one or more second screws;

(c) the first plate has one or more first holes through which the one or more first screws can be attached to the first plate and the first bone segment; and (d) the second plate has one or more second holes through which the one or more second screws can be attached to the second plate and the second bone segment.

16. The internal bone lengthener device of claim 15, wherein (a) each of the one or more first screws are a polyaxial locked screw or a monoaxial locked screw; and (b) each of the one or more second screws are a polyaxial locked screw or a monoaxial locked screw.

17. The internal bone lengthener device of claim 1 further comprising a locking mechanism to lock the first plate and second plate to prevent slidable movement along the first axis.

18. The internal bone lengthener device of claim 1, wherein each of the base, first plate, and second plate comprise a material selected from the group of titanium alloy materials.

19. The internal bone lengthener device of claim 1 further comprising a sealing material layer between the first plate and the second plate, wherein the sealing material is operable to prevent migration of body fluids of the patient or other contamination into the contained enclosure.

20. The internal bone lengthener device of claim 1, wherein the first plate and the second plate are slidably connected in a telescopic structure.

21. A method comprising the steps of:

(a) selecting an internal bone lengthening device of one of claims 1-19 or 20;

(b) fixing the internal bone lengthening device under the skin of the patient, wherein (i) a first plate of the internal bone lengthening device is fixed to a first bone segment of a patient, (ii) a second plate of the internal bone lengthening device is fixed to a second bone segment of the patient;

(c) controlling length of the internal bone lengthening device wirelessly using a remote device; and (d) obtaining feedback from the internal bone lengthening device wirelessly to monitor the length of the internal bone lengthening device.

22. The method of claim 21, wherein the internal bone lengthening device is controlled to elongate the length of the internal bone lengthening device during a bone growth process to grow bone between the first bone segment and second bone segment.

23. The method of claim 21, wherein the internal bone lengthening device is controlled to shorten the length of the internal bone lengthening device to compress soft callus during the bone growth process.

24. The method of claim 21, wherein the patient is a child.

25. The method of claim 21, wherein the feedback is displayed on a computer display.

26. The method of claim 21, wherein the feedback is analyzed to monitor patient status.

27. The method of claim 26, wherein the monitoring of patient status is performed in real time.

28. The method of claim 21 further comprising the step of uploading the feedback to a database accessible over the internet that provides a physician or other caretaker an ability to check status of the patient remotely and in real time.

29. The method of claim 21, wherein distraction rate of the internal bone lengthening device is programmable.

30. The method of claim 29, wherein the distraction rate is controllable on a basis selected from the group consisting of daily, weekly, and monthly.

* * * * *